(12) United States Patent
Elder (10) Patent No.: US 11,311,403 B2
(45) Date of Patent: Apr. 26, 2022

(54) ERECTILE DYSFUNCTION DEVICE AND METHOD

(71) Applicant: Brian Elder, Johnson Creek, WI (US)

(72) Inventor: Brian Elder, Johnson Creek, WI (US)

( * ) Notice: Subject to any disclaimer, the term of this patent is extended or adjusted under 35 U.S.C. 154(b) by 0 days.

(21) Appl. No.: 17/104,368

(22) Filed: Nov. 25, 2020

(65) Prior Publication Data

US 2021/0161699 A1 Jun. 3, 2021

Related U.S. Application Data

(60) Provisional application No. 62/942,593, filed on Dec. 2, 2019.

(51) Int. Cl.
*A61F 5/41* (2006.01)
(52) U.S. Cl.
CPC .......... *A61F 5/41* (2013.01); *A61F 2005/417* (2013.01)
(58) Field of Classification Search
CPC .................. A61F 5/41; A61F 2005/417; A61F 2005/415; A61F 2/0004; A61F 2/0009; A61F 2/0013
See application file for complete search history.

(56) References Cited

U.S. PATENT DOCUMENTS

| | | | |
|---|---|---|---|
| 3,924,634 A * | 12/1975 | Taylor | A61M 25/1002 604/100.01 |
| 3,987,789 A | 10/1976 | Timm et al. | |
| 4,483,331 A | 11/1984 | Trick | |
| 4,545,081 A | 10/1985 | Nestor et al. | |
| 4,682,592 A | 7/1987 | Thorsgard | |
| 4,869,241 A | 9/1989 | Friedmann | |
| 4,909,785 A | 3/1990 | Burton et al. | |
| 5,050,592 A | 9/1991 | Olmedo | |
| 5,445,626 A * | 8/1995 | Gigante | A61F 2/0009 600/29 |
| 5,512,033 A | 4/1996 | Westrum, Jr. et al. | |
| 5,553,379 A | 9/1996 | Westrum, Jr. et al. | |
| 5,624,395 A * | 4/1997 | Mikhail | A61M 25/10 604/99.04 |
| 5,746,222 A * | 5/1998 | Simon | A61F 2/0009 128/885 |
| 5,773,020 A | 6/1998 | Place et al. | |

(Continued)

FOREIGN PATENT DOCUMENTS

DE 102004036007 4/2006

*Primary Examiner* — Samuel G Gilbert
(74) *Attorney, Agent, or Firm* — Ryan Kromholz & Manion, S.C.

(57) ABSTRACT

A device and method for the present invention provide for an erectile dysfunction device comprising an insertion assembly in communication with a distal end cap assembly. The distal end cap assembly is positioned at a distal end of the erectile dysfunction device and external to the user's body and provides for mechanical and electronic features. The insertion assembly comprises a lumen, lumen cap and rigid section in removable communication. A proximal end of the insertion assembly is closed and provides for a lumen wall of reduced thickness. The lumen wall of reduced thickness provides for local expansion of the lumen wall to an elastic bulb when fluid is inserted in the lumen when the device is in operation by a user, the elastic bulb having an anchoring effect. A method of insertion, operation, and removal of the erectile dysfunction device is also described.

19 Claims, 6 Drawing Sheets

(56) References Cited

U.S. PATENT DOCUMENTS

| | | | |
|---|---|---|---|
| 6,102,849 | A | 8/2000 | Hakac |
| 6,579,230 | B2 | 6/2003 | Yachia et al. |
| 8,114,011 | B2 | 2/2012 | Kuyava |
| 9,968,479 | B2 | 5/2018 | Harkins, Jr. |
| 2010/0269932 | A1* | 10/2010 | Richmond ............ A61M 39/24 137/613 |

* cited by examiner

ERECTILE DYSFUNCTION DEVICE AND METHOD

RELATED APPLICATIONS

This application claims the benefit of provisional application Ser. No. 62/942,593 filed 2 Dec. 2019.

BACKGROUND OF THE INVENTION

The present invention is directed to devices which provide non-surgical aid to males having erectile dysfunction to engage in and enhance sexual intercourse and the method of operation of the device.

The prior art provides numerous and varied attempts to equip men suffering from erectile dysfunction with a solution allowing them to attain and maintain an erection required for the satisfactory completion of coitis. A majority of prior art references disclose implants to be inserted into at least one of the corpus cavernosum. These prior art references disclose the how hard it has been to provide a non-surgical solution having acceptance due to easy of application and comfortable, pleasure producing experience for both partners during intercourse.

The prior art includes clamps worn at the base of the penis which exert pressure on the veins of the penis. The clamps limit blood flow from the penis to create and sustain an erection. Other prior art references incorporate an adjustable clamp having two hinged rods that straddle the base of the penis. Elastic bands are wound around a hinge compressing and controlling pressure on both sides of the erect penis, by slowing the flow of blood from the penis.

A third prior art reference is a penile split open at both ends for the passage of bodily fluid and made to be kept at least partially in the male urethra. A plastic cap which fits over the face of the glans penis and affixed permanently to the distal end of the tube limits the progression of the tube into the penis. However, nothing is present to prevent the device from protruding from the urethra while in use, causing potential injury to one or all partners. The device possesses a condom sleeve. However, it is known in the art that condom sleeves are an unreliable form for maintaining of position.

The clamps and splint of the previously described prior art may be effective in allowing some men with erectile dysfunction to attempt sexual activity. The designs significantly reduce sensitivity of the penis. Further, the discomfort of the devices reduces the pleasure and sexual gratification for both partners.

A fourth prior art reference relates to a device which is completely insertable into the urethra. The device contains a permanent, non-retractable, bulb at the proximal end of the device. However, the non-retractable nature of the bulb may provide for discomfort during insertion and retraction of the device. Further, the complete insertion of the device does not provide for features which allow for additional and enhanced pleasure to either or both partners. Finally, due to rigid and fixed volume of the prior art, the prior art does not provide for ease of non-surgical insertion and removal.

The prior art devices rely upon external pressure or a permanent rigid insertion for accomplishing a male erection. Thus, the prior art does not allow for a pleasurable experience during the application and removal of the device from the urethra. In the case of the fourth prior art referenced, the internal nature of the prior art device requires a tool in certain scenarios for removal of the prior art device. Finally, the length of a penis is different between individuals. The non-surgical insertion devices of the prior art do not appear to provide for such variation. A penial erection device for a penis of a first length may cause discomfort to an individual whose possesses features which are less pronounced.

A need exists for an erectile dysfunction device with the capability of an expandable bulb at a proximal end of the device.

A need exists for an erectile dysfunction device providing for are internal cavity to be externally filled in order to promote erection of the male penis.

A need exists for an erectile dysfunction device providing for insertion and removal of an external fluid into the device to promote erection of the male penis.

A need exists for an erectile dysfunction device providing for an external device to promote pleasure in one or both partners.

A need exists for a method of insertion and removal of the erectile dysfunction device promoting continued pleasure and comfort in the individual.

SUMMARY OF THE INVENTION

The present invention is directed to devices which provides non-surgical aid to males having erectile dysfunction to engage in and enhance sexual intercourse and the method of operation of the device.

An erectile dysfunction device of the present invention is a non-surgical device and comprises an insertion assembly in communication with a distal end cap assembly. The distal end cap assembly is positioned at a distal end of the erectile dysfunction device. The insertion assembly has an insertion assembly distal end and an oppositely opposed insertion assembly proximal end. The insertion assembly has an insertion assembly length extending between the insertion assembly distal end and the insertion assembly proximal end. The insertion assembly proximal end is a closed end. Wherein the closed end provides a sealed barrier from entry of fluid or gas (not illustrated in the figures) into the insertion assembly, and the closed end provides a sealed barrier preventing exiting of fluid from the insertion assembly. It is understood the reference of fluid in this invention may be a liquid, gas, or a combination of a liquid and a gas.

The insertion assembly comprises a lumen in at least one of fitted and sealed communication with a lumen cap. A lumen distal end of the lumen and the lumen cap are in at least one of fitted and sealed communication at a lumen/cap communication point at or in close proximity to the insertion assembly distal end. The lumen and lumen cap are in removable communication with one another.

The lumen cap comprises lumen cap body. The lumen cap body comprises a first receiver, barrier and distal end cap assembly receiver in fixed communication with one another. When the lumen cap and lumen are in communication as previously described, a barrier second side and the opposite of the barrier first side are at least substantially perpendicular to an insertion assembly length and a lumen length defining the length of the lumen.

The first receiver extends from the barrier first side. The first receiver comprises an outer cylinder and an inner cylinder. The outer cylinder has an outer cylinder bore. The inner cylinder is positioned within the outer cylinder bore. The inner cylinder comprises an inner cylinder which defines a barrier bore positioned through the barrier. Wherein fluid may travel into the inner cylinder bore from the distal end of the erectile dysfunction device, through the barrier bore and into the distal end cap assembly receiver through the distal receiver through-bore.

The distal receiver through-bore provides for a one-way valve. A first embodiment of the one-way valve is preferably a spring valve. A second embodiment of the one-way valve is preferably a duck-bill valve. The one-way valve provides for fluid to flow from the distal end of the erectile dysfunction device and into the lumen. Specifically fluid is allowed to exit a separable syringe into and through the first receiver, and into the erectile dysfunction device, to be housed in the lumen.

A distal receiver outer surface of the distal end cap assembly receiver comprises a threaded pattern extending from the outer surface about an outer surface circumference The outer surface further comprises a graduated stepped reduction in a distal end cap assembly receiver outer diameter. The stepped reduction in the outer diameter provides for a reduced surface interference at the lumen/cap communication point. In addition, a third reduced diameter provides for the removable fitting of a rigid section on to the distal receiver proximal side.

The distal end cap assembly comprises a cap cover in threaded communication with a cap base. The cap cover is in removable communication with the cap base. A base through-bore extends from the base proximal side through the cap base and beyond the base distal side. A base through bore wall comprises a base threading pattern. The base threading pattern threadably interlocks with threaded pattern of the distal receiver outer surface. During operation of the erectile dysfunction device, the cap base is removably positioned about the lumen cap. Combination of the cap base and the lumen cap and the lumen to comprise the insertion assembly provides for the base and insertion assembly as a single unitary construction.

The cap cover comprises a parabolic cone. The cap cover and cap base are threadably compatible to removably combine the base and cap cover. The distal end of the cap assembly comprises an end cap cavity. Electronics hardware may be positioned in the end cap cavity. The electronics hardware comprises a power button/switch, at least one battery, at least one motor and at least one illumination device in electrical communication with one another. The distal end cap assembly, and thus the erectile dysfunction device, has a vibration component due to the operation of the motor. The distal end cap assembly, and thus the erectile dysfunction device, has a light emission component due to the illumination device. The vibration and the light emission act to increase pleasure for the user of the erectile dysfunction device and the partner.

The lumen comprises a lumen cavity which extends from the lumen cap at the lumen distal end towards the insertion assembly proximal end. The lumen distal end is open to receive fluid from the lumen cap. The lumen cavity extends a length which is substantially the lumen length. The lumen cavity is further defined by a lumen wall. The lumen wall has a first lumen wall thickness from the lumen distal end to a lumen wall intermediate point. Starting at the lumen wall intermediate point the lumen wall provides for at least one of a sequenced and progressive reduction in the lumen wall thickness from the first lumen wall thickness to a second lumen wall thickness in the direction of a lumen cavity proximal end. When fluid enters the lumen cavity, the graduated reduction in lumen wall thickness from the lumen wall intermediate point to the lumen cavity proximal end allows for the lumen wall to expand to an elastic bulb. Pressure from the fluid causes the elastic bulb to be created and maintained. The elastic bulb is reduced when fluid is drawn out from the lumen cap. In operation, the elastic bulb is frictionally positioned against an inner bladder wall of the bladder of the user.

The rigid section removably fixes to the distal receiver proximal side of the distal end cap assembly receiver. The rigid section extends opposite the distal end cap assembly receiver. The rigid section is a tube.

In operation of the erectile dysfunction device, the lumen is removably housed in the urethra of the user of the device by non-surgical means. The insertion assembly proximal end is positioned in a bladder of the body of the user. The elastic bulb is frictionally positioned against an inner bladder wall of the bladder to restrict movement of the erectile dysfunction device out of the body, and maintain the erectile dysfunction device within the urethra. The distal cap assembly is removably positioned against the glans of the penis. The erectile dysfunction device is filled with a fluid from a source external to the body of the user of the erectile dysfunction device. It is observed the fluid filled lumens and erectile dysfunction device promotes and maintains an erect penis for pleasurable sexual activity between the user and a partner.

The invention may be described as an apparatus for compensating erectile dysfunction, comprising: an insertion assembly having a proximal end and a distal end separated by a length, wherein the proximal end is inserted into a urethra of a penis; the insertion assembly has a lumen in communication with a lumen cap; the lumen cap is positioned at least partially beyond a glans and houses a one-way valve; and the one way valve has a direction of flow from the insertion assembly distal end to the proximal end, wherein a fluid flows into the lumen to provide for an erection of the penis.

The apparatus may further comprise: the lumen is in at least one of a fitted and a sealed communication with the lumen cap; the insertion assembly proximal end is a closed end; the lumen has a taper in close proximity to the insertion assembly proximal end; the lumen cap has a first receiver, comprising a bore defined by a wall, extended opposite the insertion assembly proximal end; the wall is frictionally compatible with at least one of a syringe and an air piston for at least one of inserting and removing the fluid within the lumen; and the one-way valve is at least one of a spring valve and a duck-bill valve.

The apparatus may further comprise: the lumen cap is in threaded communication with a distal end cap assembly, having a cover and a base; the cover and the base are in threaded communication to provide for an end cap cavity; the base has a concave surface positioned in a direction of the insertion assembly proximal end, wherein the concave surface receives the glans; the cover has a parabolic shape defining a distal end of the apparatus for compensating erectile dysfunction; the lumen cap is at least partially positioned within the end cap cavity; the end cap cavity provides for at least one of a vibration device and at least one light illuminating device; the insertion assembly proximal end providing for an elastic bulb, wherein the elastic bulb is frictionally positioned within a bladder of a user; and the lumen houses a rigid tube proximal to the lumen cap, wherein the rigid tube comprises an adjustable length.

A method of insertion, operation, and removal of the erectile dysfunction device is described. The erectile dysfunction device is manually inserted into the urethra of the penis of the user. The erectile dysfunction device is filled with a fluid from an external source. The cap cover is threadably attached to the cap base. Prior to threadably attaching the cap cover to the cap base, a user may actuate the power button/switch. The fluid in the erectile dysfunction device and the rigid section of the erectile dysfunction device promotes and maintains an erection of the penis. Actuation of the power button/switch activates vibration and light illumination from the distal end cap assembly. The vibration and light illumination promotes a pleasurable sexual experience for the user of the erectile dysfunction device and the partner. During sexual activity the size penis of the user may increase thus potentially causing an increased pressure in the body due the amount of fluid in the lumen. Fluid is drawn from the erectile dysfunction device into the syringe in order to reduce any potential discomfort resulting from use. Upon completion of sexual activity, the syringe draws fluid stored in the lumen out of the erectile dysfunction device. The drawing out of the fluid from the lumen reduces the elastic bulb to a position which allows for removal of the erectile dysfunction device from the body through the urethra. The erectile dysfunction device is non-surgically removed from the urethra, exiting the urethra at the glans.

A method of operating the apparatus for compensating erectile dysfunction, may comprise: inserting a proximal end of an insertion assembly into a urethra of a user, wherein the insertion assembly has a lumen and a lumen cap; placing at least one of a syringe and an air piston in communication with the lumen cap; transferring a fluid from at least one of the syringe and the air piston into the lumen; expanding an elastic bulb of the insertion assembly; and reversing the above steps for a removal of the insertion assembly.

The method may further comprising threading a base of a distal end cap assembly with the lumen cap; activating at least one of a vibration device and at least one light illuminating device; adjusting a quantity of the fluid in the lumen during a sexual activity by the user, wherein a size of the elastic bulb is reduced; and placing at least one of the syringe and the air piston in a friction fit communication with the lumen cap.

It is understood that the term proximal in the invention is in relation to the user's body. It is understood the term distal in the invention is in relation to the user's body.

The erectile dysfunction device of the present invention provides for the capability of an expandable bulb at a proximal end of the device.

The erectile dysfunction device of the present invention provides for an internal cavity, lumen and lumen cavity, to be externally filled in order to promote erection of the male penis.

The erectile dysfunction device of the present invention provides for insertion and removal of an external fluid into the device to promote erection of the male penis.

The erectile dysfunction device of the present invention provides for an external device, the distal cap assembly, to promote pleasure in one or both partners.

The present invention provides for a method of insertion, operation and removal of the erectile dysfunction device promoting continued pleasure and comfort in the user and partner.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is disclosed in the specification.

Figure 1:
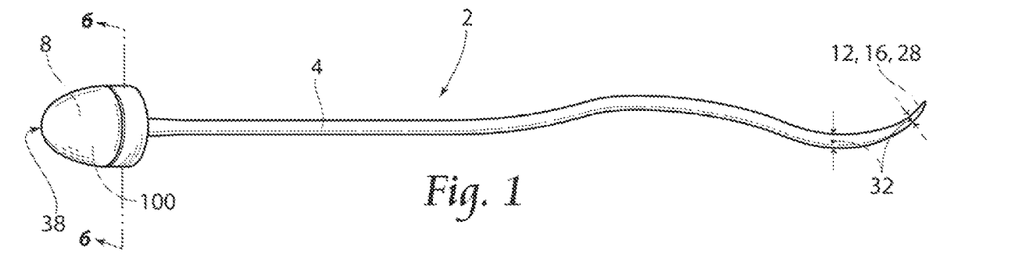
FIG. 1 is a side view of an erectile dysfunction device of this invention.
Figure 2:
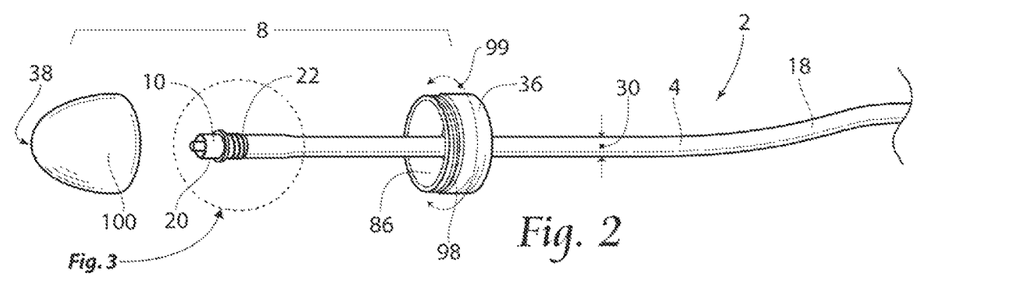
FIG. 2 is a side view of the erectile dysfunction device of this invention illustrating an exploded view of a distal end cap assembly.

With attention to FIGS. 1 and 2, an erectile dysfunction device 2 of the current invention is described. As illustrated in FIG. 2, the erectile dysfunction device 2 comprises an insertion assembly 4 in communication with a distal end cap assembly 8. The distal end cap assembly 8 is positioned at a distal end of the erectile dysfunction device 38. The insertion assembly has an insertion assembly 4 distal end 10, reference FIG. 2, and an oppositely opposed insertion assembly proximal end 12. The insertion assembly 4 has an insertion assembly length 14 extending between the insertion assembly distal end 10 and the insertion assembly proximal end 12, reference FIG. 6. As illustrated in FIG. 1, the insertion assembly proximal end 12 is a closed end 16. Wherein the closed end 16 provides a sealed barrier from entry of fluid or gas (not illustrated in the figures) into the insertion assembly 4, and the closed end 16 provides a sealed barrier from exiting of fluid or gas (not illustrated in the figures) from the insertion assembly 4. It is understood the reference of fluid in this invention may be a liquid, gas, or a combination of a liquid and a gas.

Figure 6:
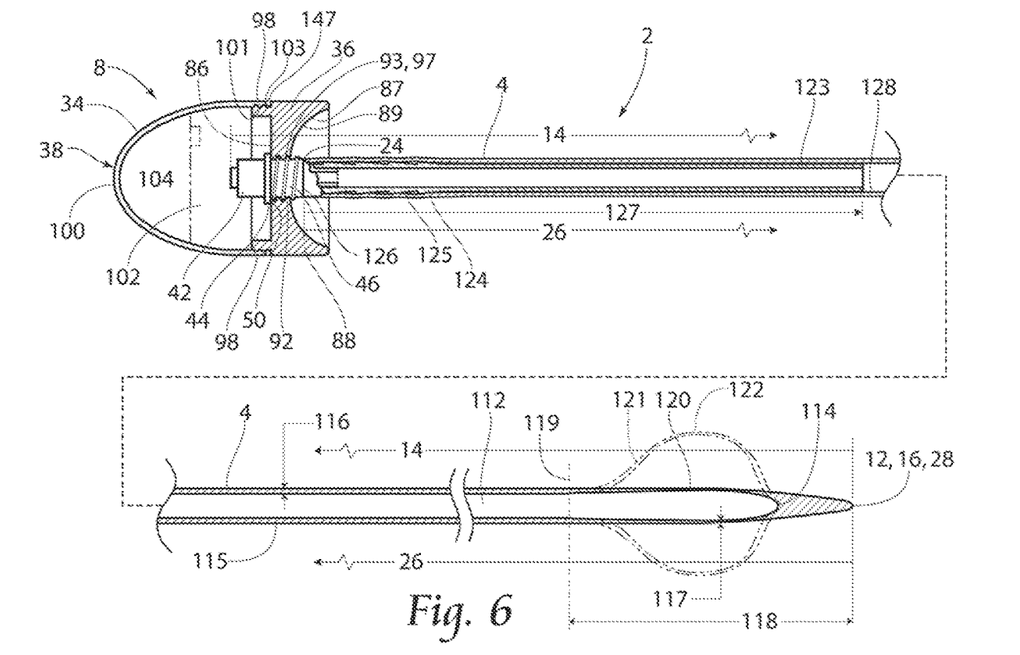
FIG. 6 is cross-section of the erectile dysfunction device of this invention.

As illustrated in FIG. 2, a side view of the erectile dysfunction device 2 of this invention illustrates an exploded view of the distal end cap assembly 8 in communication with the insertion assembly 4. The insertion assembly 4 comprises a lumen 18 in at least one of fitted and sealed communication with a lumen cap 20. The lumen 18 preferably comprises an elastic polymer material. A lumen distal and 24 (see FIG. 3) of the lumen 18 and lumen cap 20 are in at least one of fitted and sealed communication at a lumen/cap communication point 22 at or in close proximity to the insertion assembly distal end 10. As illustrated in FIGS. 1, 4 and 6, the lumen 18 comprises a lumen length 26 defined by the lumen distal end 24 and the oppositely opposed insertion assembly proximal end 12. Wherein the insertion assembly proximal end 12 is a lumen proximal end 28. The lumen 18 comprises a lumen diameter 30 extending along the lumen length 26. The lumen diameter 30 is preferably substantially constant. Further, the lumen 18 provides for a lumen tapered diameter 32 in close proximity to the lumen proximal end 28, where the lumen tapered diameter concludes at the lumen proximal end 28.

Figure 3:
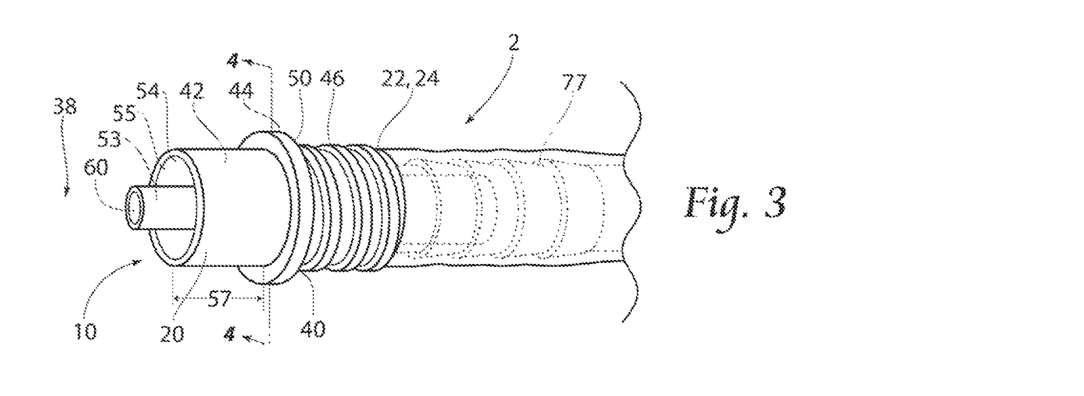
FIG. 3 is a close up view of the distal end of the insertion assembly of the erectile dysfunction device of this invention as illustrated in FIG. 2.
Figure 4:
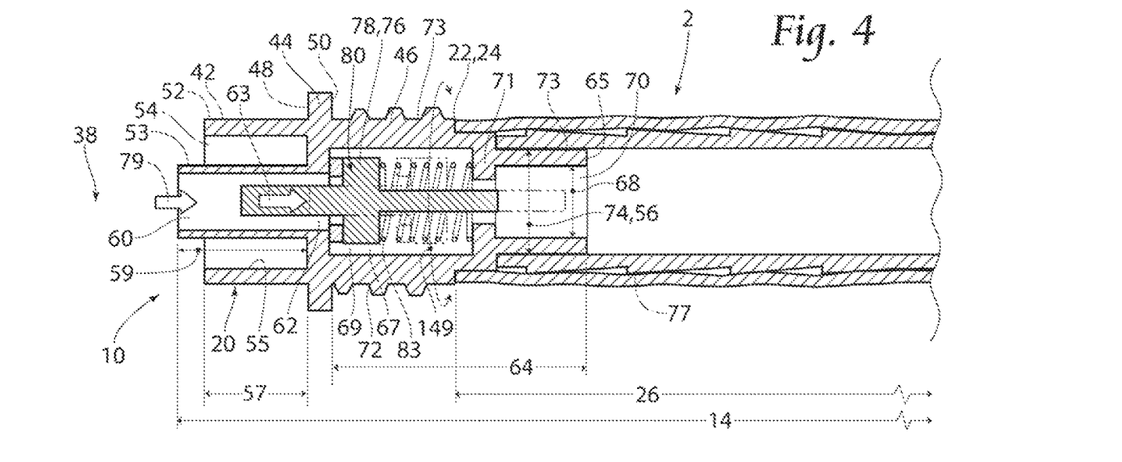
FIG. 4 is cross-section of the distal end of the insertion assembly of the erectile dysfunction device of this invention illustrating a first embodiment of a valve.
Figure 5:
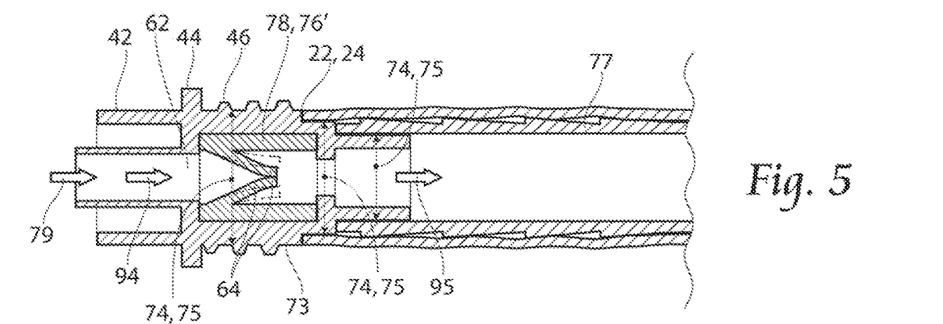
FIG. 5 is cross-section of the distal end of the insertion assembly of the erectile dysfunction device of this invention illustrating a second embodiment of the valve.

With attention to FIGS. 3, 4 and 5, the lumen cap 20 positioned at the insertion assembly distal end 10 is further described. As illustrated in FIG. 3, the lumen cap 20 comprises lumen cap body 40. The lumen cap body 40 comprises a first receiver 42, barrier 44 and distal end cap assembly receiver 46. The first receiver 42. The first receiver 42 is fixed to a barrier first aide 48. The distal end cap assembly receiver 46 is fixed to a barrier second side 50. Wherein the barrier second side 50 is opposite the barrier first side 48. The barrier 44 is interposed between the first receiver 42 and the distal end cap assembly receiver 46. When the lumen cap 20 and lumen 18 are in communication as previously described, the barrier second side 50 and the opposite the barrier first side 48 are at least substantially perpendicular to the insertion assembly length 14 and the lumen length 26, reference FIGS. 4 and 6.

The first receiver 42 extends from the barrier first side 48. The first receiver 42 comprises an outer cylinder 52 and an inner cylinder 53. The outer cylinder 52 has an outer cylinder bore 54 defined by an outer cylinder inner wall 55. When the erectile dysfunction device 2 is filled with a liquid or air, a hub 150 of a syringe 82, reference FIG. 11, and specifically an outer surface of the hub 152, reference FIG. 11, and the outer cylinder inner wall 55 are removably fractionally with one another. The removable frictional fitting of the hub 150 and outer cylinder inner wall 55 applies for removal of the liquid or air. The inner cylinder 53 is positioned within the outer cylinder bore 54. The outer cylinder 52 and inner cylinder 53 extend from the barrier 44 at least substantially parallel to one another. The outer cylinder 52 extends an outer cylinder length 57 away from the barrier 44 and the inner cylinder 53 extends an inner cylinder length 59 from the barrier 44. Preferably the inner cylinder length 59 is greater than the cuter cylinder length 57. Alternatively, the inner cylinder length 59 is substantially equal to the outer cylinder length 57. The inner cylinder 53 comprises an inner cylinder through-bore 60 extending the inner cylinder length 59. The inner cylinder through-bore 60 and the outer cylinder bore 54 extend from the barrier 44 in a direction of the distal end of the erectile dysfunction device 38. The inner cylinder bore 60 defines a barrier bore 62 positioned through the barrier 44. Wherein fluid may travel into the inner cylinder bore 60 from the distal end of the erectile dysfunction device 38, through the barrier bore 62 and into a distal receiver through-bore 67.

The distal end cap assembly receiver 46 comprises a distal receiver length 64 extending from the barrier second side 50, opposite the first receiver 42 to a distal receiver proximal side 65. The distal end cap assembly receiver 46 is a cylinder having the distal receiver through-bore 67 extending from the barrier 44 through the distal end cap assembly receiver 46 and beyond the distal receiver proximal side 65. The through-bore 67 is defined by a distal receiver inner diameter 68, where the distal receiver inner diameter provides for at least one volume and preferably two volumes, a first volume 69 and a second volume 70 separated by an internal distal receiver wall 71. At least one of the first volume 69 and the second volume 70 provides for a one-way valve 78. The one-way valve 78 provides for fluid to flow from the distal end of the erectile dysfunction device 38 and into the lumen 18, 79.

A distal receiver cuter surface 73 of the distal end cap assembly receiver 46 comprises a threaded pattern 72 extending from the outer surface 73 about an outer surface circumference 149 starting at the barrier 44 and extending along the distal receiver length 64 for a distance less than the distal receiver length 64. Preferably the threaded pattern 72 is a Luer fitting. As illustrated further in FIG. 5, the outer surface 73 further comprises a graduated stepped reduction 75 in a distal end cap assembly receiver outer diameter 74. The stepped reduction 75 in the outer diameter provides for a reduced surface interference at the lumen/cap communication point 22. In addition, a third reduced diameter 56 provides for the fitting of a rigid section 77 on to the distal receiver proximal side 65.

Figure 11:
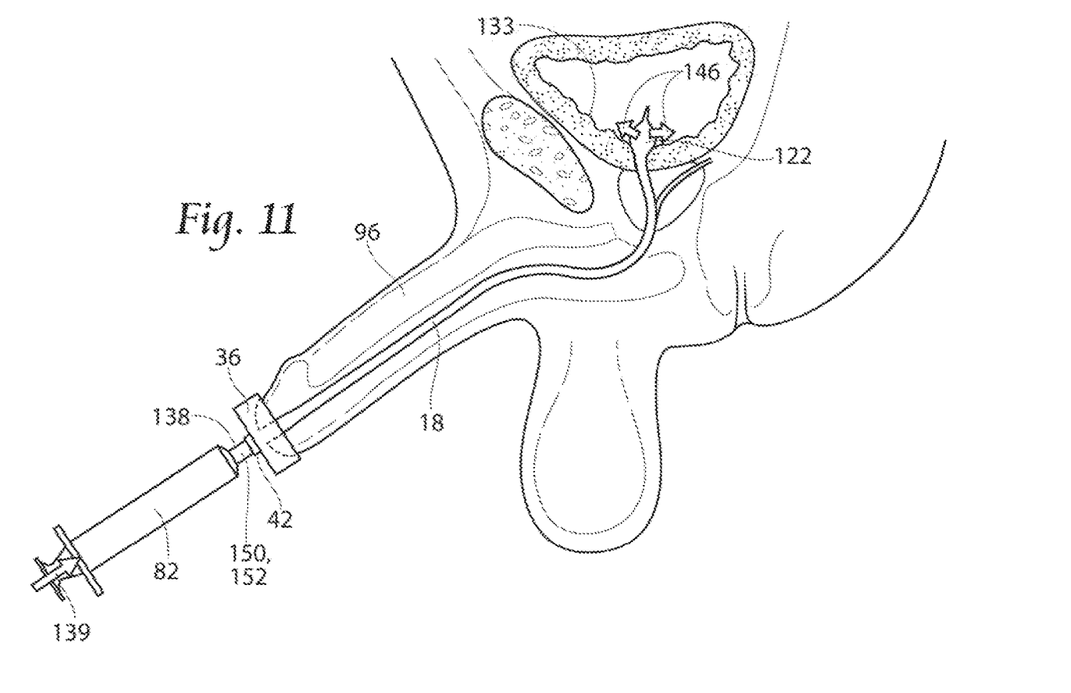
FIG. 11 is a method of operation of the erectile dysfunction device of this invention illustrating filling the internal volume of a lumen of the insertion assembly with a volume.

As illustrated in FIG. 4, a first embodiment of the one-way valve 76 is provided. The first embodiment of the one-way valve 76 is preferably a spring valve. A syringe 82, reference FIG. 11, is placed into the inner cylinder bore 60 and contacts a valve insert 80. The valve insert 80 is in removable and sealed communication with a distal end inner surface 91. The distal end inner surface 91 defining the distal receiver through-bore 60. Specifically, the valve insert 80 provides for removable sealing of the barrier bore 62. The removable sealing of the barrier bore 62 provides for a barrier preventing fluid to pass into and out of the distal end cap assembly receiver 46, and thus maintaining a volume of liquid in the lumen 18. A spring mechanism 83 is positioned between the valve insert 80 and the internal distal receiver wall 71, and in contact with at least one of the valve insert 80 and the internal distal receiver wall 71. The spring mechanism 83 is in an extended position to provide for a sealed communication between the valve insert 80 and the distal end inner surface 91. A syringe 82 is removably positioned on the valve insert 80. Advancement of the syringe 82 in the direction of the lumen proximal end 28, reference FIGS. 1 and 6, causes the spring mechanism 83 to constrict the of the first embodiment of the one-way valve 76, moving the valve insert 80 towards the lumen proximal end 28, reference FIGS. 1 and 6. Wherein fluid is allowed to exit the syringe 82 and into the erectile dysfunction device 2 to be housed in the lumen 18, 79.

As illustrated in FIG. 5, a second embodiment of the one-way valve 76' is provided. The second embodiment of the one-way valve 76' is preferably a duck-bill valve. A syringe 82, reference FIG. 11, is placed into the inner cylinder bore 60. Contents, fluid, of the syringe 82 are released into the lumen cap 20 in the direction of the second embodiment of the one-way valve 76', 94. The contents force the valve flaps 84 to provide separation between the respective valve flaps 84 allowing the fluid to further enter the erectile dysfunction device 2 to be housed in the lumen 18, 95. Wherein fluid is allowed to exit the syringe 82 and into the erectile dysfunction device 2 to be housed in the lumen 18, 79

As illustrated in FIGS. 1, 2 and 6, the distal end cap assembly 8 comprises a cap cover 34 in threaded communication with a cap base 36. The cap cover 34 is in removable communication with the cap base 36 such that the distal end cap 8 assembly comprises the two components which may be attached and removed from one another repeatedly. The cap base 36 preferably comprises a cylindrical shape 88. The cylindrical shape 88 is defined by a base distal side 86 and an oppositely opposed base proximal side 87. The proximal side 87 comprises a concave surface 89 in the direction of the opposite base distal side 86. The concave surface 89 of the proximal side 87 removably receives the glans 90 of the penis 96 of the user of the erectile dysfunction device 2. A base through-bore 92 extends from the base proximal side 87 through the cap base 36 and beyond the base distal side 86. The base through-bore 92 is defined by a base through bore wall 93 extending from the base proximal side 87 to the base distal side 86. The base through-bore wall 93 comprises a base threading pattern 97. The base threading pattern 97 is preferably a Luer fitting. The base threading pattern 97 threadably interlocks with threaded pattern 72 of the distal receiver outer surface 73. As further illustrated in FIG. 2, the cap base 36 is in slidable communication with the lumen 18. Specifically, the lumen 18 is in slidable communication with the base through-bore wall 93.

During operation of the erectile dysfunction device 2, the cap base 36 is removably positioned about the lumen cap 20. Wherein the base threading pattern 97 threadably and removably interlocks with threaded pattern 72 of the distal receiver outer surface 73. The base distal side 86 is positioned against the barrier second side 50, wherein the barrier second side 50 provides a stop for the further advancement of the cap base 36 towards the distal end of the erectile dysfunction device 38. Combination of the base 36, the lumen cap 20 and the lumen 18 provides for the base 36 and insertion assembly 4 as a single unitary construction.

As further illustrated in FIGS. 1, 2 and 6, about the base distal side 86 or extended from the base distal side 86, the base 36 comprises a second base threading pattern 98 about a base circumference 99. The cap cover 34 comprises a parabolic cone 100. At a cone base 103, the parabolic cone 100 comprises a cone threading 101. The cone threading 101 and second base threading pattern 98 are threadably compatible to removably combine the base 36 and cap cover 34. The distal end cap assembly 8 comprises the threadably combined base 36 and cap cover 34. Combination of the cap cover 34 and the base 36, which is removably combined to the insertion assembly 4, provides for the distal end cap assembly 3 and the insertion assembly 4 as a single unitary construction. An annular O-ring 147 is positioned between the cone base 103 and the base 36 to provide for a sealed fitting between the cap cover 34 and the base 36. The sealed fitting of the annular O-ring 147 keeps fluids and gases external to the erectile dysfunction device 2 from entering a distal end cap cavity 102 of the distal end cap assembly 8 during sexual activity.

The distal end cap assembly 8 comprises the end cap cavity 102, specifically the threadable combination of the base 36 and cap cover 34 defines the end cap cavity 102. The first receiver 42 is positioned in the end cap cavity 102 when the distal end cap assembly 8 and the insertion assembly 4 are in threaded communication. Electronics hardware 104 is positioned in the end cap cavity 102.

Figure 7:
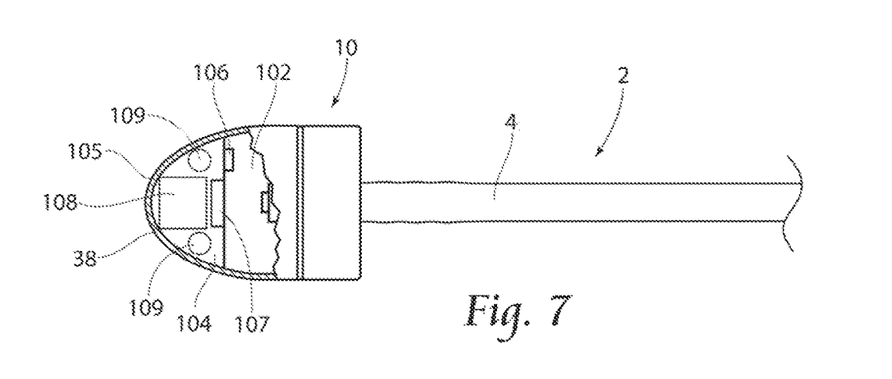
FIG. 7 is cross-section of the distal end cap assembly of the erectile dysfunction device of this invention.

With attention to FIGS. 6 and 7, the electronics hardware 104 is further described. The electronics hardware 104 is preferably positioned at an end cap cavity at distal end 105 of the end cap cavity 102, where the end cap cavity distal end 105 is positioned opposite the cap base 36 when the cap base 36 and cap cover 34 are threadably combined. Alternatively, the electronics component is positioned along a predetermined surface of the distal end cap assembly 8 which defines the end cap cavity 102. The electronics hardware 104 may comprise a power button/switch 106, at least one battery 107 (or power source), at least one motor 108 and at least one illumination device 109 in electrical communication with one another. Prior to threadably combining the cap base 36 and cap cover 34, a user may actuate the power button/switch 106. The resulting communication between the at least one battery 107, the at least one motor 108 and the at least one illumination device 109 provides for activation of at least one of the motor 108 and the illumination device 109. The distal end cap assembly 8, and thus the erectile dysfunction device 2, has a vibration 110, reference FIG. 11, due to the operation of the motor. The distal end cap assembly 8, and thus the erectile dysfunction device 2, has a light emission 111 due to the illumination device 109. The vibration 110 and the light emission 111 act to increase pleasure for the user of the erectile dysfunction device 2 and the partner.

With attention to FIG. 6, the lumen 18 is further described. The lumen 18 comprises a lumen cavity 112 which extends from the lumen cap 20, at lumen distal end 24, towards the insertion assembly proximal end 12. The lumen distal end 24 is open to receive fluid from the lumen cap 20. The lumen cavity 112 has extends the length which is substantially the lumen length 26. The lumen cavity 112 terminates in close proximity to the insertion assembly proximal end 12, between the insertion assembly proximal end 12 and the lumen cap 20, at a lumen cavity proximal end 114. The lumen cavity 112 is further defined by a lumen wall 115. The lumen wall 115 has a first lumen wall thickness 116 from the lumen distal end 24 to a lumen wall intermediate point 119. The lumen wall intermediate point 119 is between the lumen distal point 24 and the lumen cavity proximal end 114. The lumen wall intermediate point 119 is a lumen bulb distance 118 from the lumen cavity proximal end 114. Starting at the lumen wall intermediate point 119 the lumen wall provides for at least one of a sequenced and progressive reduction in the lumen wall thickness from the first lumen wall thickness 116 to a second lumen wall thickness 117. When fluid enters the lumen cavity 112 from the lumen cap 20, as previously described. The lumen wall 115 between the lumen wall intermediate point 119 and the lumen cavity proximal end 114 has a progressively reduced thickness, from the lumen wall intermediate point 119 and the lumen cavity proximal end 114, allowing for the lumen wall 115 to expand along the lumen bulb distance 118. Specifically, fluid entering the lumen cavity 112 expands the lumen wall 115 along the lumen bulb distance 118. The lumen wall 155 comprises an elastic wall 120 along the lumen bulb distance 118 due to the reduced wall thickness of the lumen wall 112 from the first thickness 116 to the second thickness 117. The elastic wall 120 has a graduated effect 121 from the lumen wall intermediate point 119 to the lumen cavity proximal end 114, wherein the elastic wall 120 possesses greater elasticity in close proximity to the lumen cavity proximal end 114. The greater elasticity 121 reduces along the lumen bulb distance 118 in the direction of the lumen wall intermediate point 119. The elastic wall 120 is filled with fluid entering from the lumen cap 20, and the fluid filled elastic wall 120 between the lumen wall intermediate point 119 and the lumen cavity proximal end 114 comprises an elastic bulb 122. Pressure from the fluid causes the elastic bulb 122 to be created and maintained. The elastic bulb 122 is reduced when fluid is drawn out from the lumen cap 20, reducing the volume of fluid in the lumen 18.

With attention to FIGS. 3, 4, and 6, the rigid section is further described. As previously observed, the third reduced diameter 56 of the distal end cap assembly receiver 46 provides for the fitting of the rigid section 77 on to the distal receiver proximal side 65. The rigid section 77 preferably comprises a semi-rigid polymer material having an elasticity less than the polymer material comprising the lumen 18 and having an elasticity less than a flaccid penis 96. The rigid section 77 extends opposite the distal end cap assembly receiver 46. The rigid section 77 is a tube 123. The rigid section 77 comprises a progressive annular ridges 124 about a rigid section exterior surface 125. The annular ridges 124 are positioned in close proximity to a rigid section first end 126. The rigid section first end 126 is in communication with the distal end cap assembly receiver 46. The rigid section 77 has a predetermined rigid section length 127. The rigid exterior surface 125 is in contact with the lumen wall interior surface 128, which defines the lumen cavity 112. The progressive annular ridges 124 are in frictional contact with the lumen wall interior surface 128 providing for maintaining the position of the lumen 18 and the rigid section 77 with respect to one another.

Figures 8, 9:
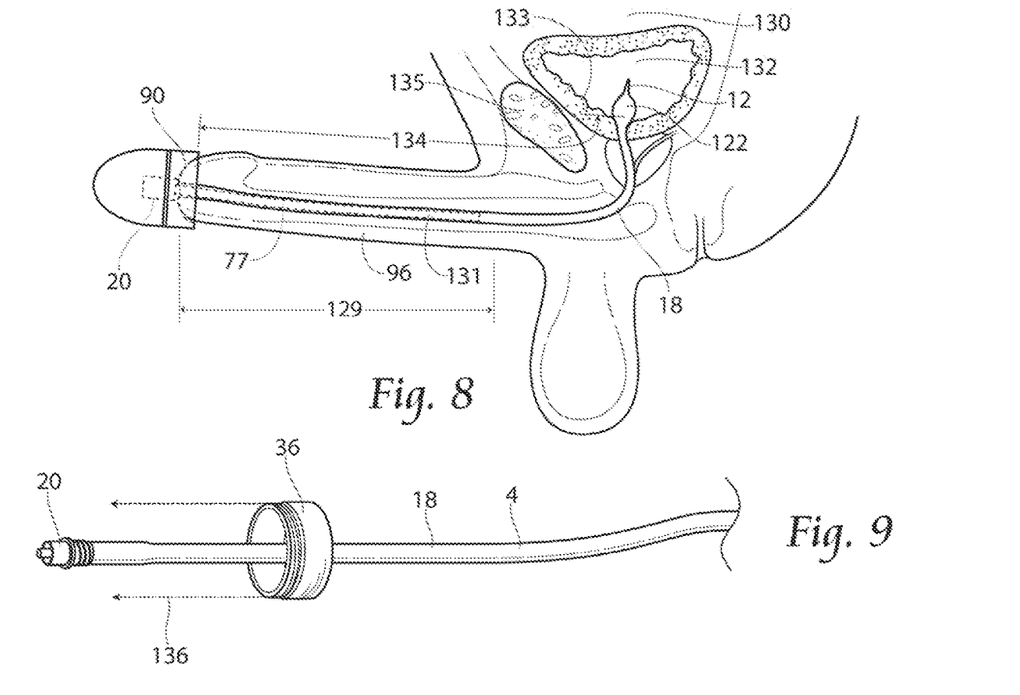
FIG. 8 is a preferred embodiment of the erectile dysfunction device of this invention positioned in the male body.
FIG. 9 is a method of operation of the erectile dysfunction device of this invention illustrating placing a base of the distal end cap assembly in communication with the insertion assembly.

With attention to FIG. 8, the erectile dysfunction device 2 is described in operation in a body 130 of a user of the device 2. The lumen 18 is removably housed in the urethra 131 of the user of the device 2. The insertion assembly proximal end 12 is positioned in a bladder 132 of the body 130 of the user. The elastic bulb 122 is frictionally positioned against an inner bladder wall 133 of the bladder 132. The frictional position of the elastic bulb 122 against the inner bladder wall 133 restricts movement of the erectile dysfunction device 2 out of the body 130, and maintains the erectile dysfunction device 2 within the urethra 131. The distal cap assembly 8 is removably positioned against the glans 90 of the penis 96. Wherein the distal cap assembly 8 extends from the glans 90 such that the distal cap assembly 8 is positioned externally with respect to the penis 96 and the body 130 in general. The glans to bladder length 134 varies between users of the erectile dysfunction device 2 thus the graduated effect 121 of the elastic bulb 122 provides for the device 2 to accommodate for varying glans to bladder lengths 134 because the elastic bulb 122 will reduce expansion once the elastic bulb 122 has expanded to frictionally contact the inner bladder wall 133. The rigid section 77 has a rigid section length 127 at least substantially equal to a penis length 129. It is understood the penis length 129 varies between users. Thus, the rigid section length 127 may be mechanically altered by cutting of the rigid section 77 to provide for a rigid section 77 having a rigid section length 127 which terminates prior to the pelvic bone 135. It is observed the fluid filled lumens 18 and erectile dysfunction device 2 promotes and maintains an erect penis 96 for sexual activity between the user and a partner.

Figure 10:
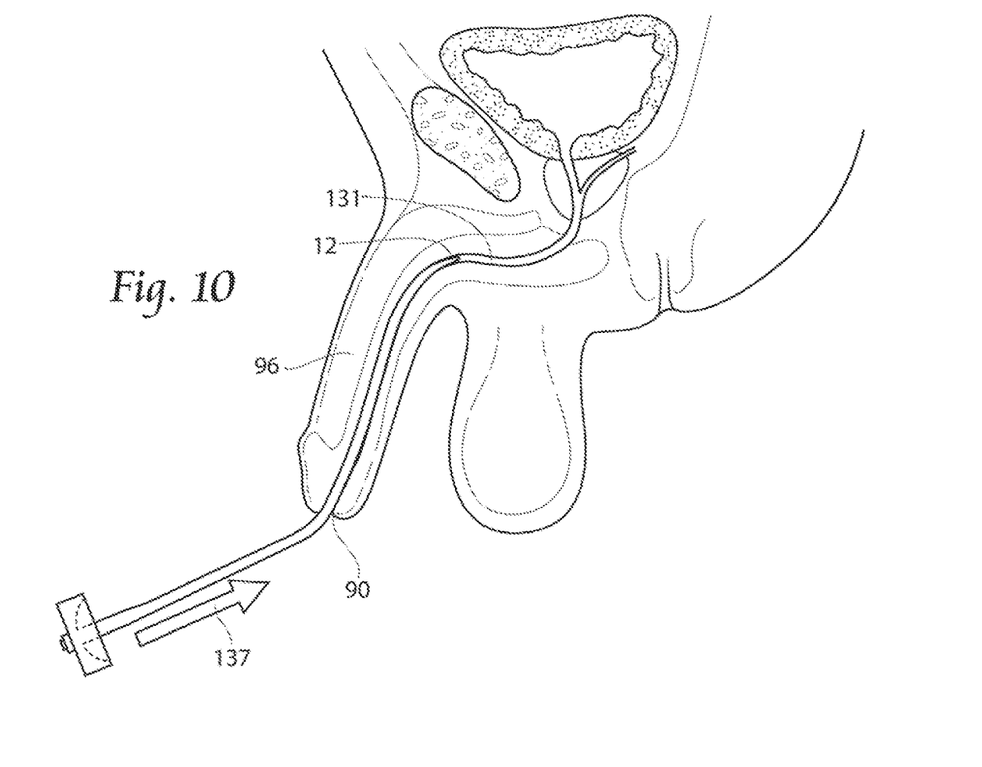
FIG. 10 is a method of operation of the erectile dysfunction device of this invention illustrating insertion of a proximal end of the insertion assembly into the male urethra.

With attention to FIGS. 9, 10, 11, 12, 13, 14, 15, 16 and 17, the method of operating the erectile dysfunction device 2 is described. As illustrated in FIG. 9, the cap base is 36 is slidably positioned about the lumen 18 and positioned threadably in communication with the lumen cap 20, 136. As illustrated in FIG. 10, the insertion assembly proximal end 12 is inserted into the urethra 131 at the glans 90, and manually maneuvered through the urethra 131 until the glans 90 is in contact with the cap base 36, 137. As illustrated in FIG. 11, the syringe 82, and specifically the hub 150 of the syringe 62, is placed in insertable communication with the first receiver 42, 138. In doing so, the outer surface of the hub 152 of at least a portion of the hub 150 is placed in contact with the outer cylinder inner wall 55, reference FIG. 4. The contact between the hub surface 152 and the outer cylinder inner wall 55, reference FIG. 4, is a removable friction fit. Alternatively, an air piston may be used in place of the syringe 62, and thus the communication between the air piston and outer cylinder inner wall 55 may be a removable friction fit. The fluid in the syringe 62 is promoted or transferred into the first receiver 42 and subsequently the lumen 18, 139. Advancement of the fluid through the lumen 18 expands the elastic bulb 122, wherein the elastic bulb 122 becomes frictionally positioned against the inner bladder wall 133, 146. Therein, the syringe 82 or air piston is removed from the frictional fit with the outer cylinder inner wall 55.

Figure 12:
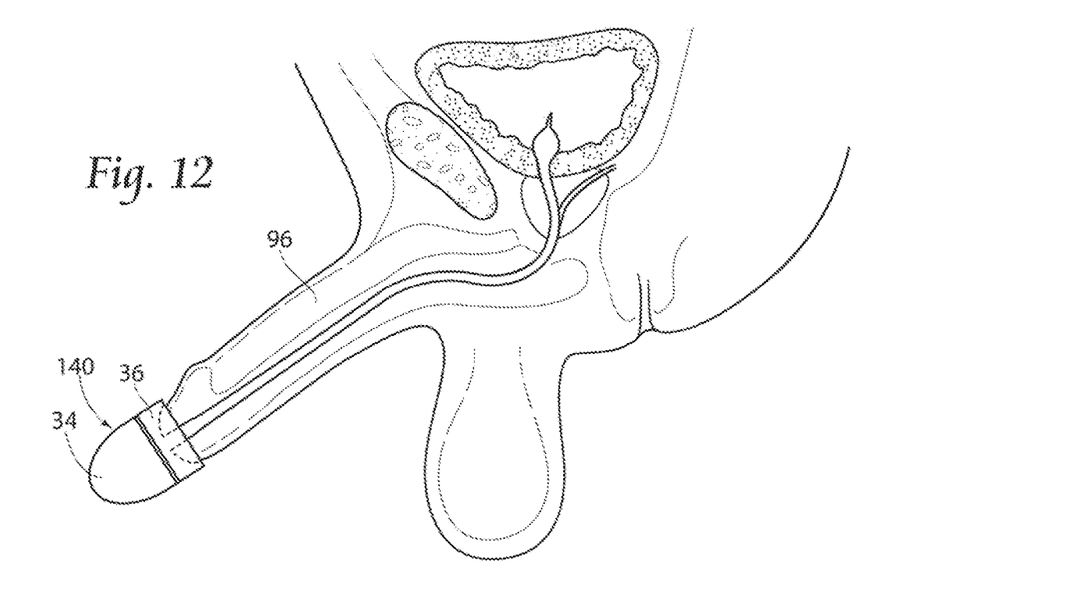
FIG. 12 is a method of operation of the erectile dysfunction device of this invention illustrating placing a cap cover in communication with the base of the distal end cap assembly.
Figure 13:
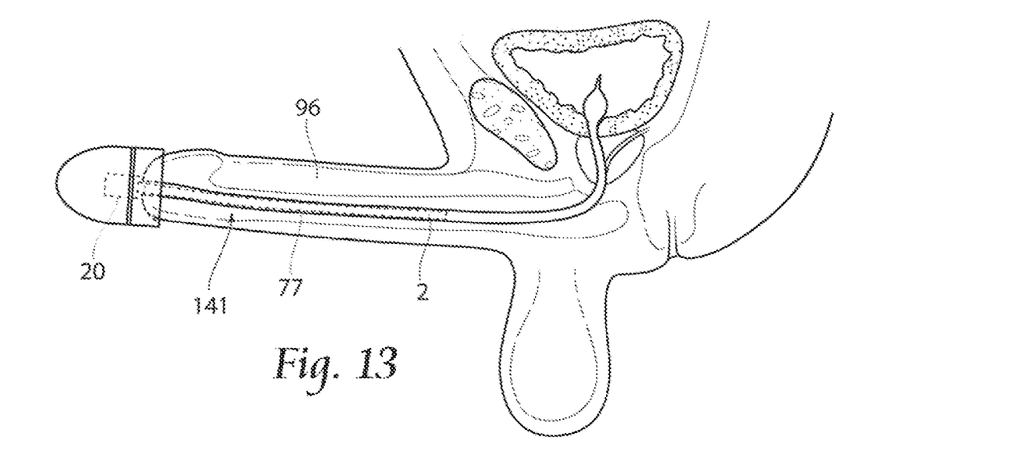
FIG. 13 is a method of operation of the erectile dysfunction device of this invention illustrating erection of the penis.
Figure 14:
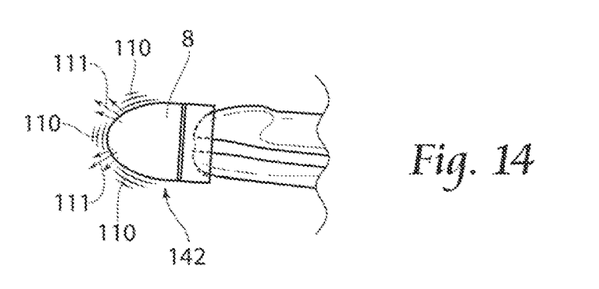
FIG. 14 is a method of operation of the erectile dysfunction device of this invention illustrating at least one of vibration and illumination of the distal end cap assembly.
Figure 15:
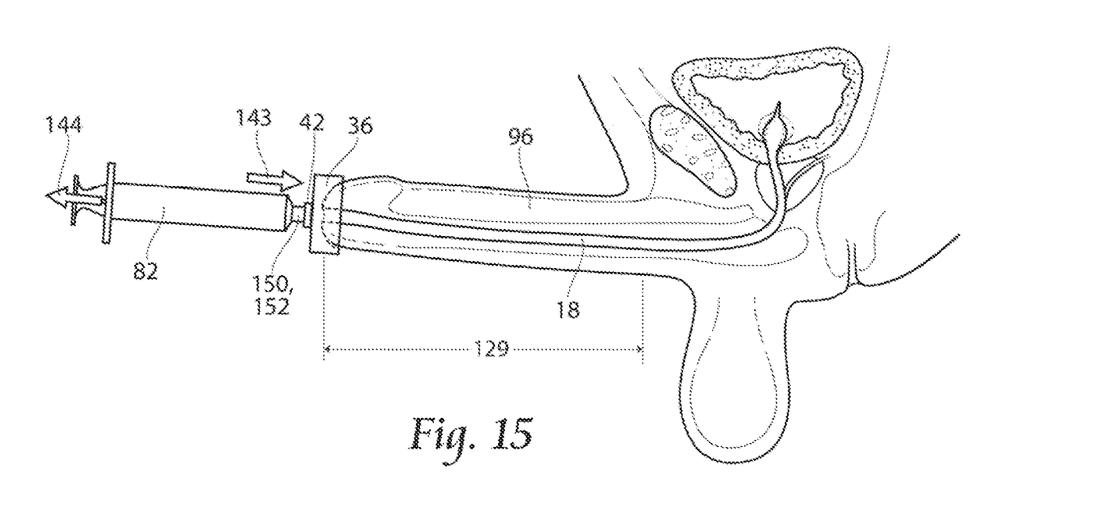
FIG. 15 is a method of operation of the erectile dysfunction device of this invention illustrating regulation of the liquid in the internal volume of the lumen of the insertion assembly.
Figure 16:
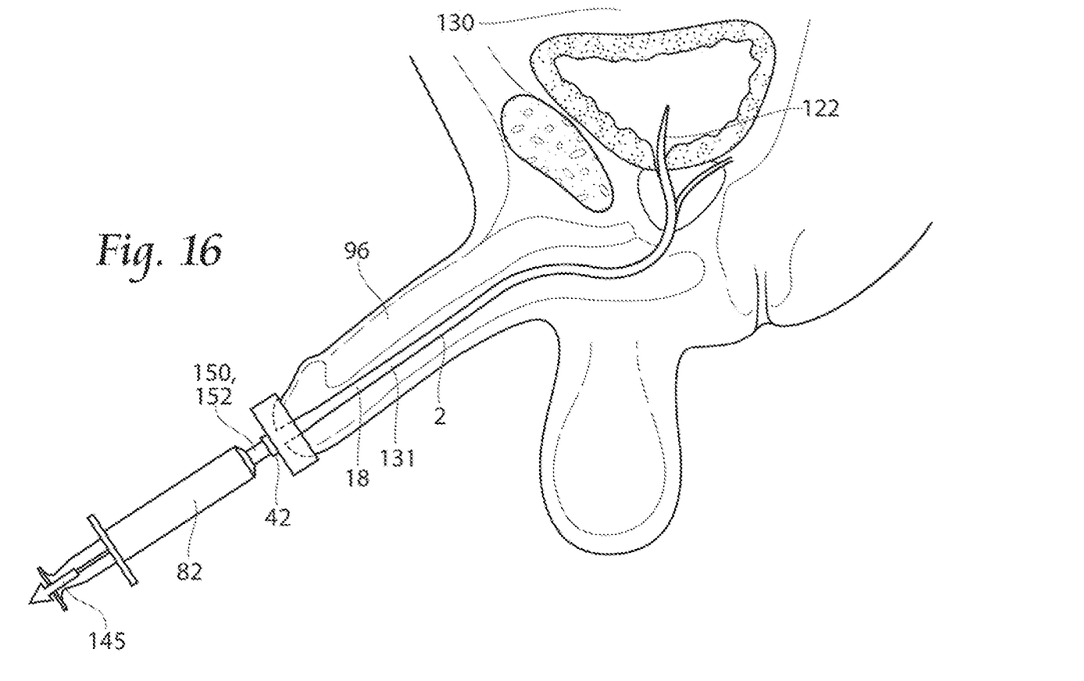
FIG. 16 is a method of operation of the erectile dysfunction device of this invention illustrating removal of the liquid from the internal volume of the lumen of the insertion assembly.
Figure 17:
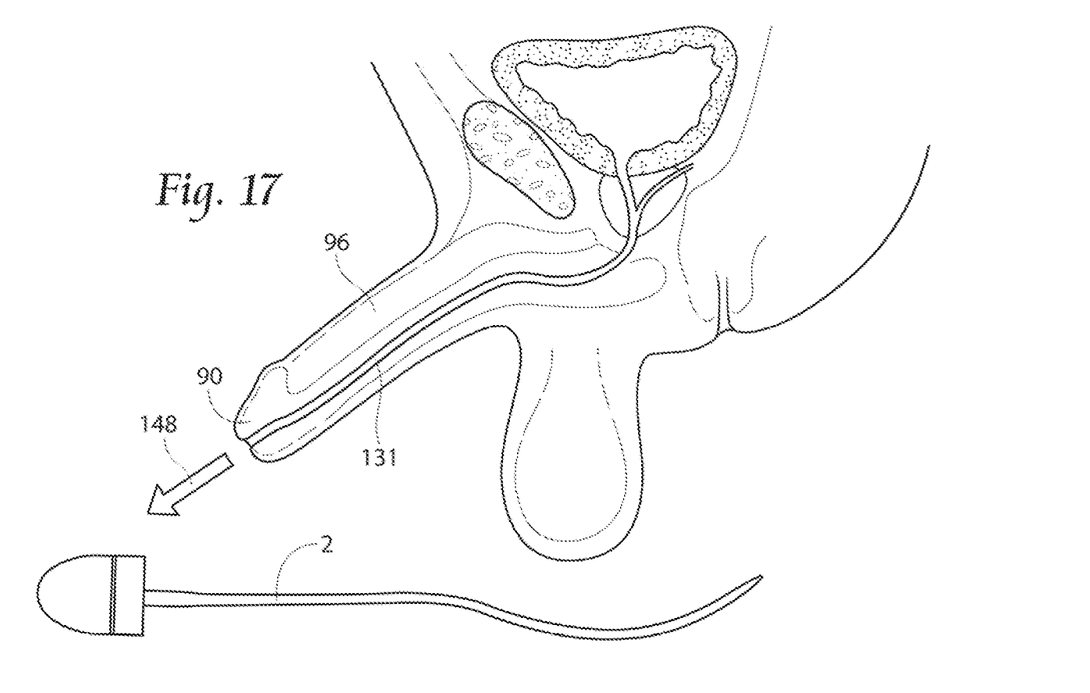
FIG. 17 is a method of operation of the erectile dysfunction device of this invention illustrating removal of the erectile dysfunction device from the urethra of the penis.

As illustrated in FIG. 12, the cap cover 34 is threadably attached to the cap base 36, 140. Prior to threadably attaching the cap cover 34 to the cap base 36, a user may actuate the power button/switch 106, reference FIG. 7. As illustrated in FIG. 13, the fluid in the erectile dysfunction device 2 and the rigid section 77 of the erectile dysfunction device 2 promotes and maintains an erection of the penis 96, 141. As illustrated in FIG. 14, actuation of the power button/switch 106, reference FIG. 7, activates at least one of vibration 110 and light illumination 111 from the distal end cap assembly 8, 142. At least one of the vibration 110 and light illumination 111 promotes a pleasurable sexual experience for the user of the erectile dysfunction device 2 and the partner. As illustrated in FIG. 15, during sexual activity the penis length 129 may increase thus potentially causing an increased pressure in the body 130 due the amount of fluid in the lumen 18. The cap cover 34 is removed and the syringe 82 is placed in communication with the first receiver 42, as previously described, 143. Fluid is drawn from the erectile dysfunction device 2 into the syringe 82 in order to reduce any potential discomfort resulting from use, 144. Following removal of a specified amount of fluid, the cap cover 34 is again placed in threadable communication with the cap base 36 and sexual activity is resumed. In drawing out the fluid, the elastic bulb 122 is reduced in size, see FIG. 15 where the elastic bulb 122, as referenced in FIG. 11, is reduced in size allowing for an increased penis length 129. As illustrated in FIG. 16, upon completion of sexual activity, the syringe 82 is again placed in communication with the first receiver 42, as previously described. The syringe 82 draws fluid stored in the lumen 18 out of the erectile dysfunction device, 145. The drawing out of the fluid from the lumen 18 reduces the elastic bulb 122 to a position which allows for removal of the erectile dysfunction device 2 from the body 130 through the urethra 131. As illustrated in FIG. 17, the erectile dysfunction device 2 is removed from the urethra 131, exiting the urethra 131 at the glans 90, 148.

It is understood that the term proximal in the invention is in relation to the body 130. It is understood the term distal in the invention is in relation to the body 130.

At least one aspect of the first embodiment of the one-way valve 76 may be combined with at least one aspect of the second embodiment of the one-way valve 76'.

The erectile dysfunction device 2 of the present invention provides for the capability of an expandable bulb 122 at a proximal end 12 of the device 2.

The erectile dysfunction device 2 of the present invention provides for an internal cavity, lumen 18 and lumen cavity 112, to be externally filled in order to promote erection of the male penis 96.

The erectile dysfunction device 2 of the present invention provides for insertion and removal of an external fluid into the device 2 to promote erection of the male penis 96.

The erectile dysfunction device 2 of the present invention provides for an external device, the distal cap assembly 8, to promote pleasure in one or both partners.

The present invention provides for a method of insertion, operation and removal of the erectile dysfunction device 2 promoting continued pleasure and comfort in the user and partner.

The foregoing is considered as illustrative only of the principles of the invention. Furthermore, since numerous modifications and changes will readily occur to these skilled in the art, it is not desired to limit the invention to the exact construction and operation shown and described. While the preferred embodiment has been described, the details may be changed without departing from the invention, which is disclosed in the specification.

I claim:

1. An apparatus for insertion into a urethra of a penis for compensating erectile dysfunction, comprising:
   an insertion assembly having a proximal end and a distal end separated by a length, wherein said proximal end is adapted to be inserted into said urethra of said penis;
   said insertion assembly having a lumen in communication with a lumen cap;
   said lumen cap positioned at least partially beyond a glans and housing a one-way valve;
   said lumen housing a rigid tube proximal to said lumen cap; and
   said one-way valve having a direction of flow from said insertion assembly distal end to said proximal end, said proximal end being a closed end, wherein a fluid flows into said lumen to provide for an erection of said penis.

2. The apparatus of claim 1, further comprising said lumen is in at least one of a fitted and a sealed communication with said lumen cap.

3. The apparatus of claim 1, further comprising said lumen having a taper in close proximity to said insertion assembly proximal end.

4. The apparatus of claim 1, further comprising said lumen cap having a first receiver, comprising a bore defined by a wall, extended opposite said insertion assembly proximal end.

5. The apparatus of claim 4, further comprising said wall is frictionally compatible with at least one of a syringe and an air piston for at least one of inserting and removing said fluid within said lumen.

6. The apparatus of claim 1, further comprising said one-way valve is at least one of a spring valve and a duck-bill valve.

7. The apparatus of claim 1, wherein said rigid tube comprises an adjustable length.

8. The apparatus of claim 1, further comprising said lumen cap is in threaded communication with a distal end cap assembly, having a cover and a base.

9. The apparatus of claim 8, wherein said cover and said base are in threaded communication to provide for an end cap cavity.

10. The apparatus of claim 9, wherein said lumen cap is at least partially positioned within said end cap cavity.

11. The apparatus of claim 9, wherein said end cap cavity contains at least one of a vibration device and at least one light illuminating device.

12. The apparatus of claim 8, further comprising said base having a concave surface positioned in a direction of said insertion assembly proximal end, wherein said concave surface is adapted to receive said glans.

13. The apparatus of claim 8, further comprising said cover having a parabolic shape defining a distal end of said apparatus for compensating erectile dysfunction.

14. The apparatus of claim 1, further comprising said insertion assembly proximal end providing for an elastic bulb, wherein said elastic bulb is adapted to be positioned within a bladder of a user.

15. A method of operating an apparatus for insertion into a urethra of a penis for compensating erectile dysfunction, comprising:
    inserting a closed proximal end of an insertion assembly into a urethra of a user, said insertion assembly having a lumen, housing a rigid tube, and a lumen cap;
    placing at least one of a syringe and an air piston in communication with said lumen cap;
    transferring a fluid from at least one of said syringe and said air piston into said lumen;
    expanding an elastic bulb of said insertion assembly, wherein said rigid tube and said fluid compensate for said erectile dysfunction for sexual function; and
    removing said apparatus through reducing said elastic bulb and removing said proximal end from said user.

16. The method of claim 15, further comprising placing at least one of said syringe and said air piston in a friction fit communication with said lumen cap.

17. The method of claim 15, further comprising threading a base of a distal end cap assembly with said lumen cap.

18. The method of claim 15, further comprising activating at least one of a vibration device and at least one light illuminating device, enclosed b said lumen cap.

19. The method of claim 15, further comprising adjusting a quantity of said fluid in said lumen during a sexual activity by said user, wherein a size of said elastic bulb is reduced.

* * * * *